United States Patent
Schatz

(10) Patent No.: US 11,273,274 B1
(45) Date of Patent: Mar. 15, 2022

(54) INHALATION DELIVERY DEVICE AND METHOD OF USE

(71) Applicant: Thilo Schatz, Baldwin Park, CA (US)

(72) Inventor: Thilo Schatz, Baldwin Park, CA (US)

(*) Notice: Subject to any disclaimer, the term of this patent is extended or adjusted under 35 U.S.C. 154(b) by 594 days.

(21) Appl. No.: 16/195,401

(22) Filed: Nov. 19, 2018

Related U.S. Application Data

(60) Provisional application No. 62/594,443, filed on Dec. 4, 2017.

(51) Int. Cl.
| | |
|---|---|
| *A61M 16/00* | (2006.01) |
| *G05B 19/042* | (2006.01) |
| *A61M 11/04* | (2006.01) |
| *A61M 11/00* | (2006.01) |
| *A61M 16/06* | (2006.01) |
| *A61M 16/10* | (2006.01) |

(52) U.S. Cl.
CPC ........ *A61M 16/024* (2017.08); *A61M 11/005* (2013.01); *A61M 11/042* (2014.02); *A61M 16/0003* (2014.02); *A61M 16/0672* (2014.02); *A61M 16/0683* (2013.01); *A61M 16/1005* (2014.02); *G05B 19/042* (2013.01); *A61M 2016/0027* (2013.01); *A61M 2202/0208* (2013.01); *A61M 2205/0216* (2013.01); *A61M 2205/0294* (2013.01); *A61M 2205/3331* (2013.01); *A61M 2205/3368* (2013.01); *A61M 2205/3584* (2013.01); *A61M 2205/50* (2013.01); *A61M 2205/7545* (2013.01); *A61M 2205/8206* (2013.01); *A61M 2209/088* (2013.01); *G05B 2219/25252* (2013.01)

(58) Field of Classification Search
CPC .............. A61M 16/06; A61M 16/0666; A61M 16/0672; A61M 16/0683; A61M 16/0085; A41D 13/1107; A41D 13/1115
See application file for complete search history.

(56) References Cited

U.S. PATENT DOCUMENTS

| | | | |
|---|---|---|---|
| 6,390,453 B1 | 5/2002 | Frederickson et al. | |
| 8,281,787 B2 | 10/2012 | Burton | |
| 8,714,158 B2 | 5/2014 | Hernandez et al. | |
| 9,211,388 B2 | 12/2015 | Swift et al. | |
| 2001/0042546 A1* | 11/2001 | Umeda | A61M 16/06 128/206.21 |
| 2012/0174922 A1* | 7/2012 | Virr | A62B 23/025 128/203.12 |
| 2014/0158136 A1 | 6/2014 | Romagnoli et al. | |
| 2014/0261413 A1 | 9/2014 | Gibson | |
| 2015/0157822 A1* | 6/2015 | Karpas | B29C 33/52 128/206.24 |
| 2015/0314095 A1 | 11/2015 | Himes, Jr. et al. | |

(Continued)

FOREIGN PATENT DOCUMENTS

| | | | |
|---|---|---|---|
| DE | 102006039115 A1 | 3/2008 | |
| FR | 2707884 A1 | 1/1995 | |

(Continued)

*Primary Examiner* — Margaret M Luarca
(74) *Attorney, Agent, or Firm* — Procopio Cory Hargreaves and Savitch LLP

(57) ABSTRACT

A wearable inhalation delivery device comprising a wearable member that is securable to a wearer's head; and an inhalation delivery device carried by the wearable member and configured to deliver fluid to the wearer's air passages upon inhalation.

18 Claims, 7 Drawing Sheets

(56) References Cited

U.S. PATENT DOCUMENTS

| | | | |
|---|---|---|---|
| 2015/0320960 A1 | 11/2015 | Barlow et al. | |
| 2016/0310686 A1 | 10/2016 | Salmon et al. | |
| 2016/0375205 A1 | 12/2016 | Cressman | |
| 2018/0078798 A1* | 3/2018 | Fabian | ............... A61B 5/6803 |

FOREIGN PATENT DOCUMENTS

| | | | | |
|---|---|---|---|---|
| KR | 101703922 | * | 2/2017 | |
| KR | 101703922 B1 | * | 2/2017 | ............. A62B 18/02 |
| KR | 101753668 B1 | | 7/2017 | |

* cited by examiner

INHALATION DELIVERY DEVICE AND METHOD OF USE

CROSS REFERENCE TO RELATED APPLICATIONS

This application claims the benefit under 35 U.S.C. 119(e) of U.S. Provisional Patent Application Ser. No. 62/594,443, filed Dec. 4, 2017, and entitled "VAPE MASK AND METHOD OF USE," which is incorporated herein by reference in its entirety as if set forth in full.

FIELD OF THE INVENTION

The present invention relates to inhalation delivery devices positionable for use on a wearer's face.

SUMMARY OF THE INVENTION

An aspect of the invention is a wearable inhalation delivery device to be positioned for use on the wearer's face. Inhalation of air through a wearers nose or mouth, depending on the type of inhalation delivery device, activates the wearable inhalation delivery device, delivering a fluid (e.g., aerosol, vapor, mist, oxygen gas), which enters the wearer's air passages. In an embodiment of the device, the device is contained within an air pollution protection mask featuring layers of particulate filters. As used herein, a fluid is a substance that has no fixed shape and yields easily to external pressure such as a gas and/or liquid. Examples of fluids mentioned herein that may be delivered include aerosol, vapor, mist, and oxygen gas.

Another aspect of the invention involves a wearable inhalation device comprising a wearable member that is securable to a wearer's head; and an inhalation delivery device carried by the wearable member and configured to deliver a fluid such as, but not limited to, aerosol, vapor, mist, or oxygen gas, to the wearer's air passages upon inhalation.

Implementations of the aspect of the invention described immediately above include one or more of the following: the wearable member is a mask; the mask includes a lower-face covering section with opposite side including elastic ear bands configured to go over and behind a wearer's ears to secure the mask over a lower part of a wearer's face; the wearable member includes opposite sides, a central portion between the opposite sides, and laterally and horizontally extending pockets that extend in opposite directions laterally and horizontally from the central portion to the opposite sides; the inhalation delivery device includes opposite laterally and horizontally extending leg members carried within the laterally and horizontally extending pockets of the wearable member; the inhalation delivery device includes a nose pillow with a nasal opening; the inhalation delivery device includes a mouthpiece; the inhalation delivery device includes opposite laterally extending leg members comprising a first leg member having a supply; the first leg member includes a side with a flexible opening that the supply is removably insertable within; the first leg member has a cylindrical disk-shaped receiving section and the supply includes a cylindrical disk-shaped head that is received within the cylindrical disk-shaped receiving section of the first leg member to retain the supply in the first leg member; the inhalation delivery device includes opposite laterally extending leg members comprising a second leg member having an electronics pack; the second leg member includes an open end that the electronics pack is removably insertable within; the inhalation delivery device includes an air pressure sensor, a power source, and a microprocessor configured to deliver a fluid such as aerosol, vapor, mist, or oxygen gas to the wearer's air passages upon detection of inhalation by the air pressure sensor, the inhalation delivery device includes a vape tank with a vape heating coil, the microprocessor configured to determine coil temperature based in part on measured resistance of the vape heating coil and control the power source to adjust supply of power to the heating coil to control an amount of vape delivered; the inhalation delivery device includes a tank and a vaporizing nozzle, and the microprocessor is configured to control the vaporizing nozzle to control an amount of fluid released from the tank; the inhalation delivery device includes an oxygen tank and a mechanism to release oxygen from the oxygen tank, and the microprocessor is configured to control the mechanism to control an amount of oxygen released from the oxygen tank; the inhalation delivery device includes a fluid tank and an ultrasonic piezoelectric transducer, and the microprocessor is configured to control the ultrasonic piezoelectric transducer to control an amount of fine mist released from the fluid tank; the air pressure sensor is configured to measure inhalation pressure and deliver the fluid such vapor, aerosol, mist, or oxygen gas if the microprocessor determines if the inhalation pressure has at least met a minimum predetermined inhalation pressure to deliver fluid; and/or the inhalation delivery device includes electronics and a module coupled with the microprocessor to allow functionality control of the inhalation delivery device via a mobile app on a mobile computing device.

DETAILED DESCRIPTION

Figure 1:
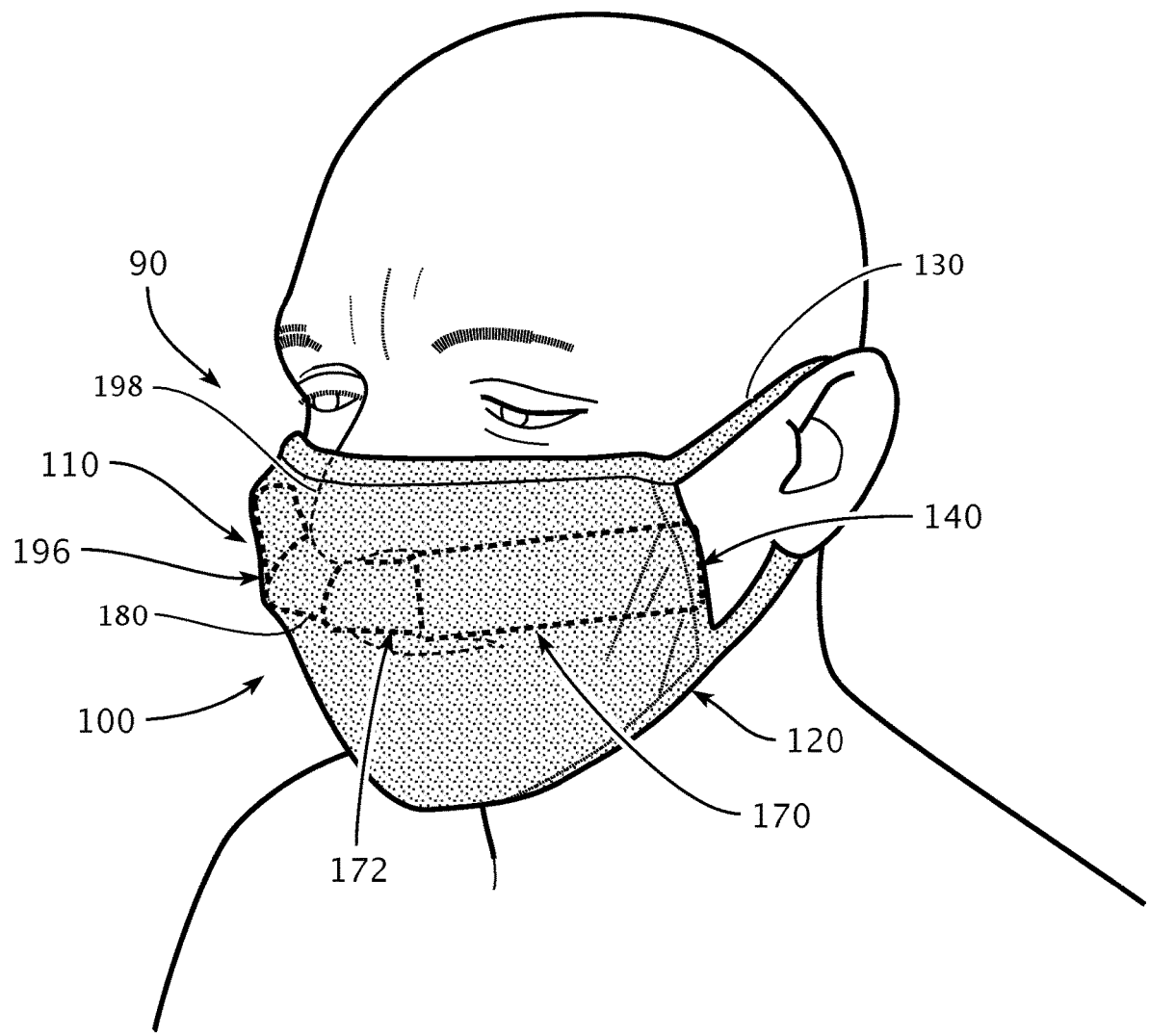
FIG. 1 is a rear elevational view of an embodiment of a wearable inhalation delivery device installed in the mask.

With reference to FIGS. 1-7, an embodiment of a wearable inhalation delivery device 90 including a mask 100 with an inhalation delivery device ("device") 110 installed in the mask 100 and method of use will be described.

The mask 100 includes a lower-face covering section 120 with elastic ear bands 130 extending from opposite sides 140 that go over and behind a wearer's ears to secure the mask 100 over the lower part of a wearers face. The lower-face covering section 120 includes a mouth section, which may include a filter that may include layers of particulate filters. The lower-face covering section 120 includes laterally/horizontally extending pockets 170 that extend in opposite directions laterally/horizontally from a central portion 172 to the opposite sides 140.

The device 110 includes an inhalation delivery mechanism 180 such as, but not limited to, the shown silicone nasal/nose pillow with a nasal opening 190 therein. The nasal opening 190 may include a filter 192. Protuberances 194 are a thickening of the silicone on opposite sides of the nasal opening 190, creating two points of contact with the wearers face, on both sides of the wearers upper lip. These protuberances 194 allow a central/middle portion 196 of the device 110 with the nasal opening 190 directed towards a wearer's nose 198 to "float" over the upper lip, allowing the upper lip to move freely during speech and allows for any other mouth/lip/nose movement during the breathing process. The nasal pillow is designed to allow for comfortable breathing (inhalation/exhalation primarily through the nasal passages) and will have a partial seal with nose to enable the wearer to breath and speak normally.

Figure 6:
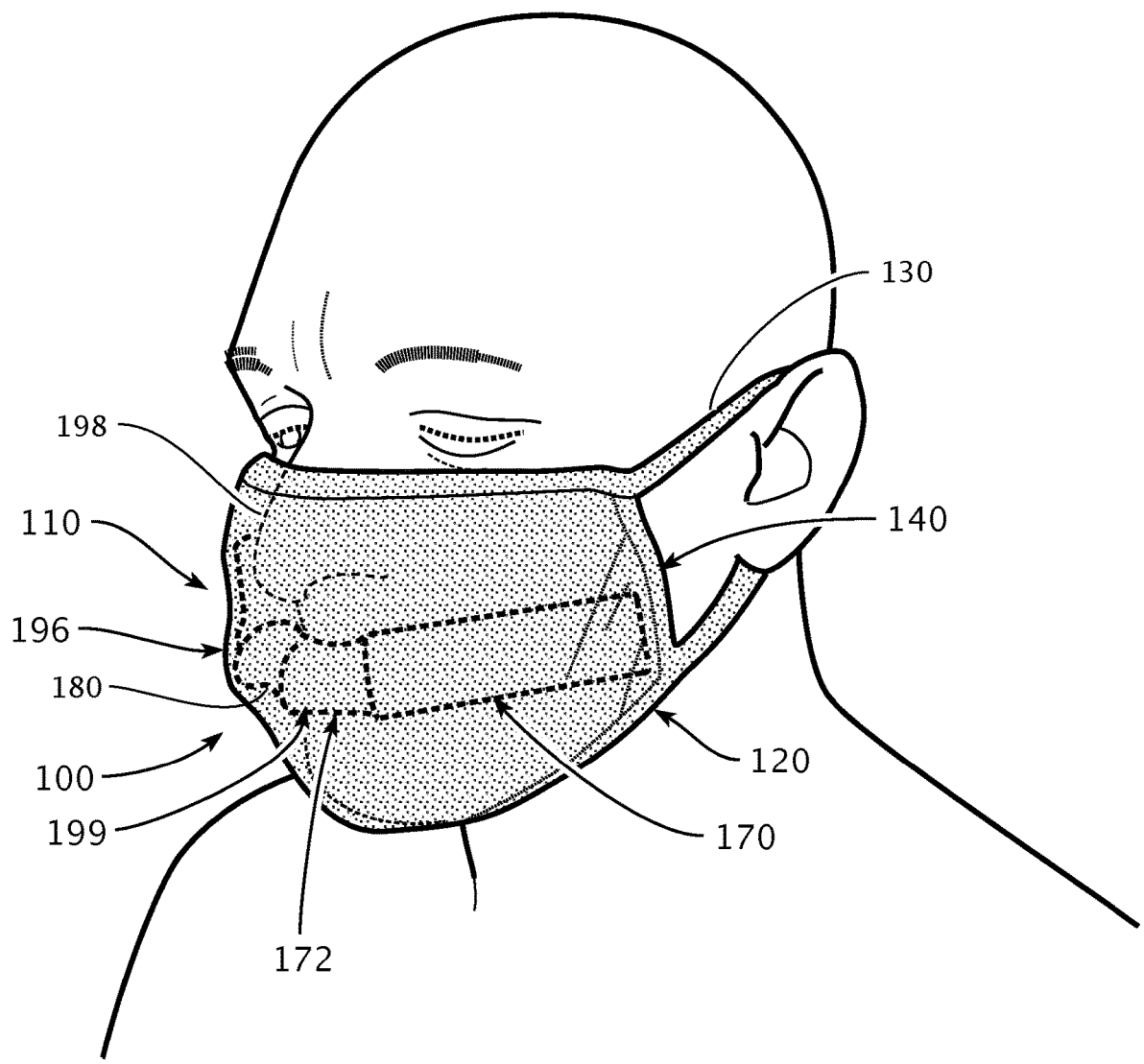
FIG. 6 is a rear elevational view of another embodiment of a wearable inhalation delivery device of FIG. 2.

With reference to FIG. 6, in an alternative embodiment, the inhalation delivery mechanism 180 includes a mouthpiece 199 for inhalation/exhalation primarily through the oral cavity instead of through the nasal passages.

In a further embodiment, the inhalation delivery mechanism 180 includes both the nose pillow with nasal opening 190 and the mouthpiece 199.

Figure 2:
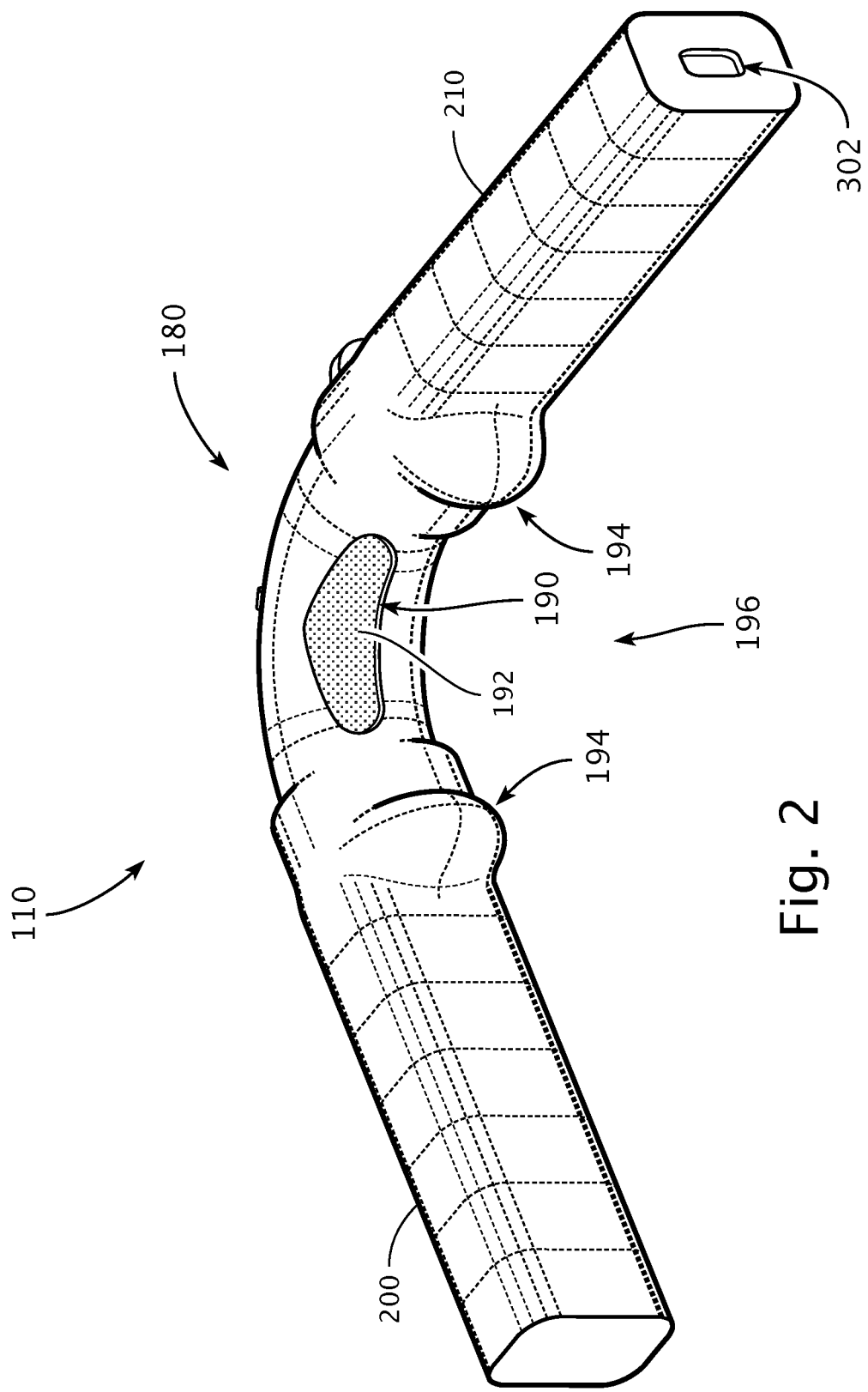
FIG. 2 is a rear elevational view of an embodiment of an inhalation delivery device of the wearable inhalation delivery device of FIG. 1 shown removed from the mask.
Figure 3:
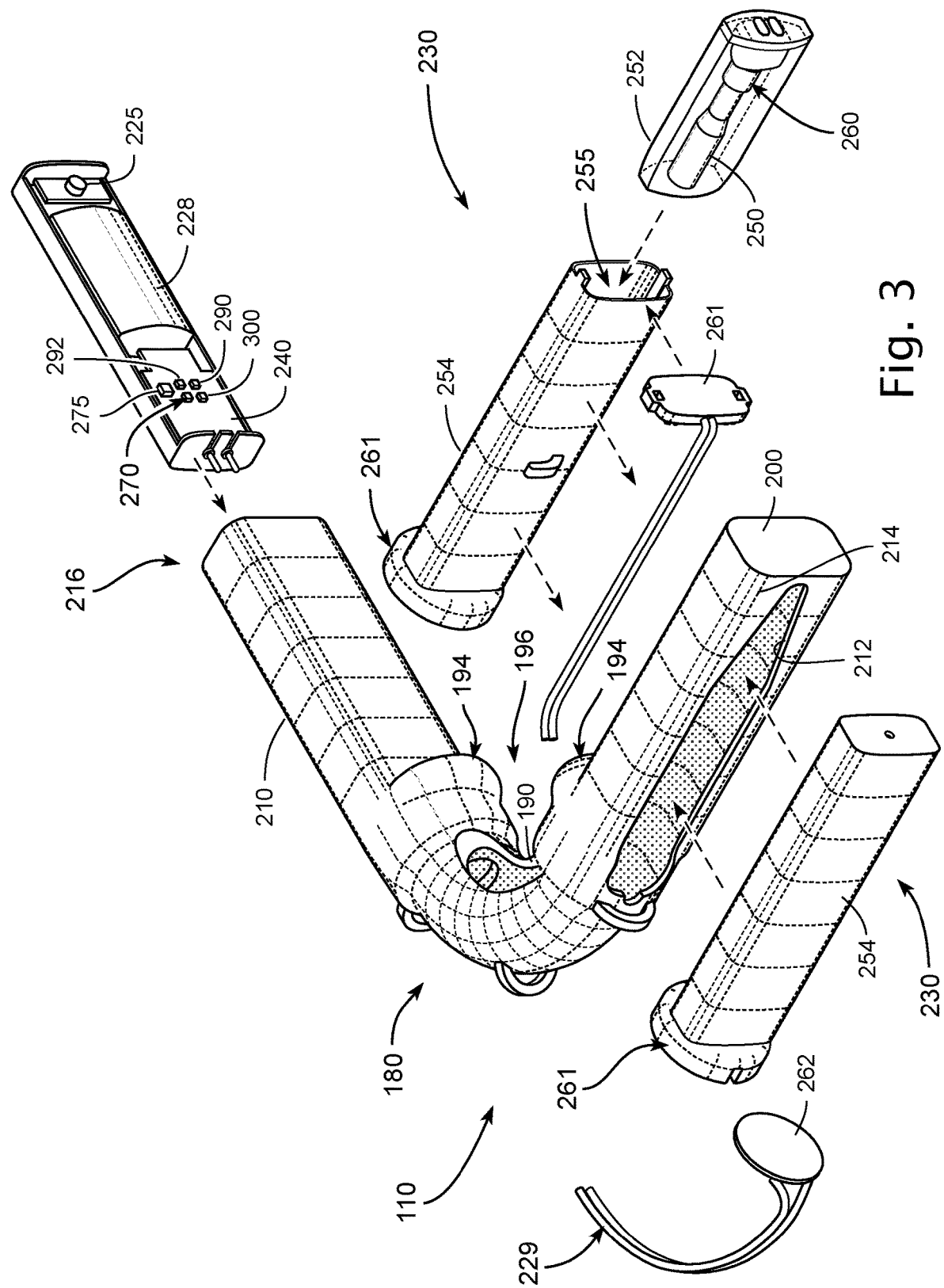
FIG. 3 is an exploded perspective view of the inhalation delivery device of FIG. 2.
Figure 4:
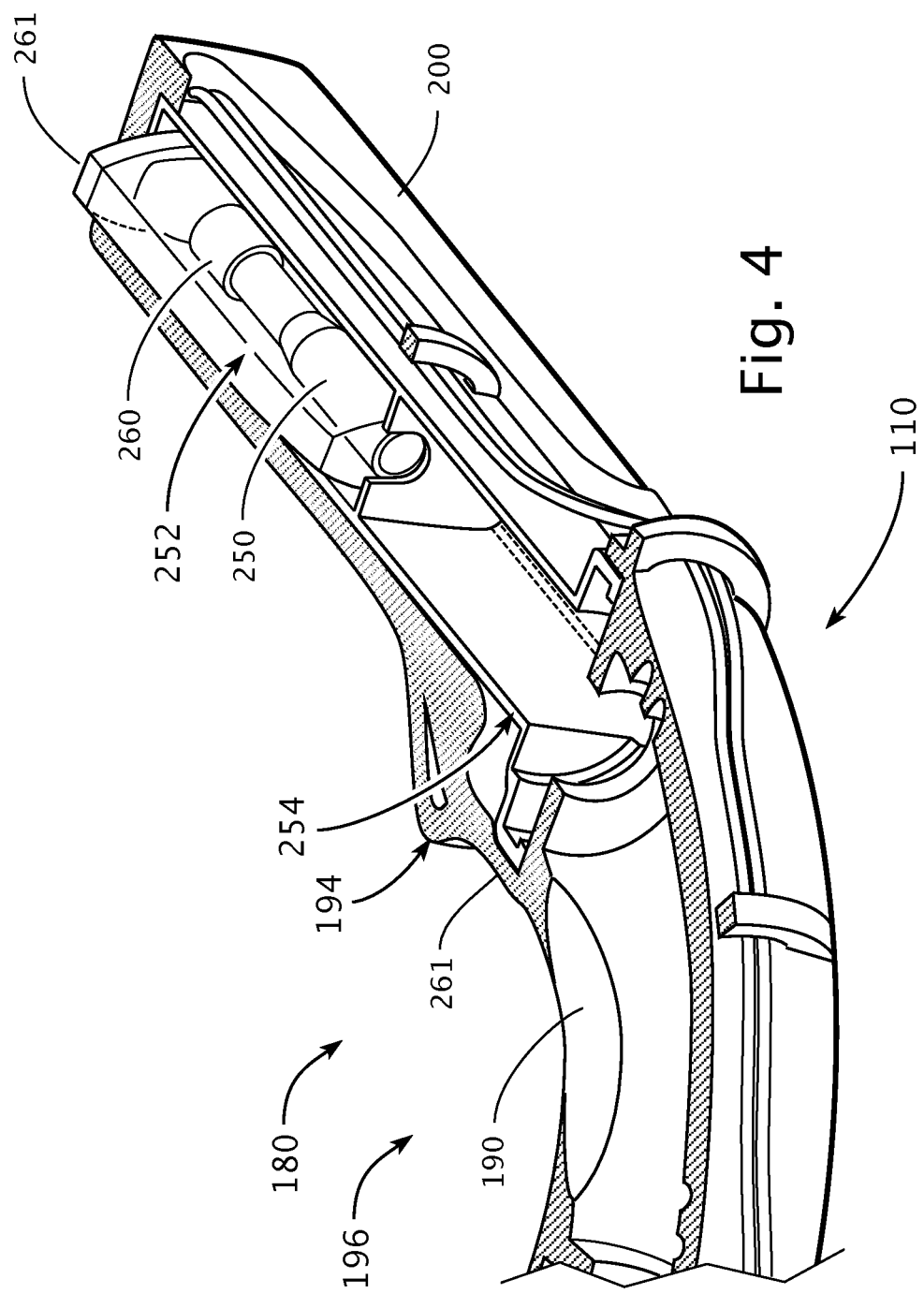
FIG. 4 is a partial cut-away perspective view of the inhalation delivery device of FIG. 2.

The inhalation delivery mechanism 180 bridges opposite first and second laterally/horizontally extending leg members 200, 210. As shown in FIGS. 2-4, the first leg member 200 includes a flexible opening 212 along a side 214 that a liquid storage (e.g., vape tank/pack, tank/pack, ultrasonic nebulizer tank/pack) 230 may be removably insertable within. The second leg member 210 includes an open end 216 that a removably insertable electronics pack/components 218 may be inserted through, into the second laterally extending leg member 210. The electronics pack 218 includes one or more of an air pressure sensor 225, a battery/power source 228, and a circuit board 240. The first and second laterally/horizontally extending leg members 200, 210 are removably insertable in the laterally/horizontally extending pockets 170 of the mask 100.

In the position shown in FIG. 1, the inhalation delivery mechanism 180 is disposed laterally/horizontally across a front of the wearers face, below the wearer's nose 198, with the central/middle portion 196 of the device 110 with the nasal opening 190 directed towards a wearer's nose 198 to "float" over the upper lip. The design of the inhalation delivery mechanism 180 allows for a universal fit and to be comfortable when wearing for long period of time.

In an alternative embodiment, the wearable inhalation deliver device 90 shown in FIGS. 2-6 does not include the mask 100.

As shown in FIGS. 3 and 4, in an embodiment where the liquid storage/supply in the first leg member 200 is a vape tank/pack 230, the pack 230 includes a vape wick cylinder 250 that may be part of a removable cartridge 252 that is removably insertable in a removable housing/tank 254 through an open bottom 255. The vape tank/pack 230 includes a vape heating coil 260 that is electrically coupled to the battery 228 via electrical connection assembly 261.

In an embodiment where the liquid storage/supply in the first leg member 200 is an tank/pack 230, the pack 230 may include an electromechanical device (e.g., mechanical gear and miniature electro motor driven device that is controlled and powered by the electronics pack 218 to puncture or control a valve on the tank to produce an aerosol.

Figure 5:
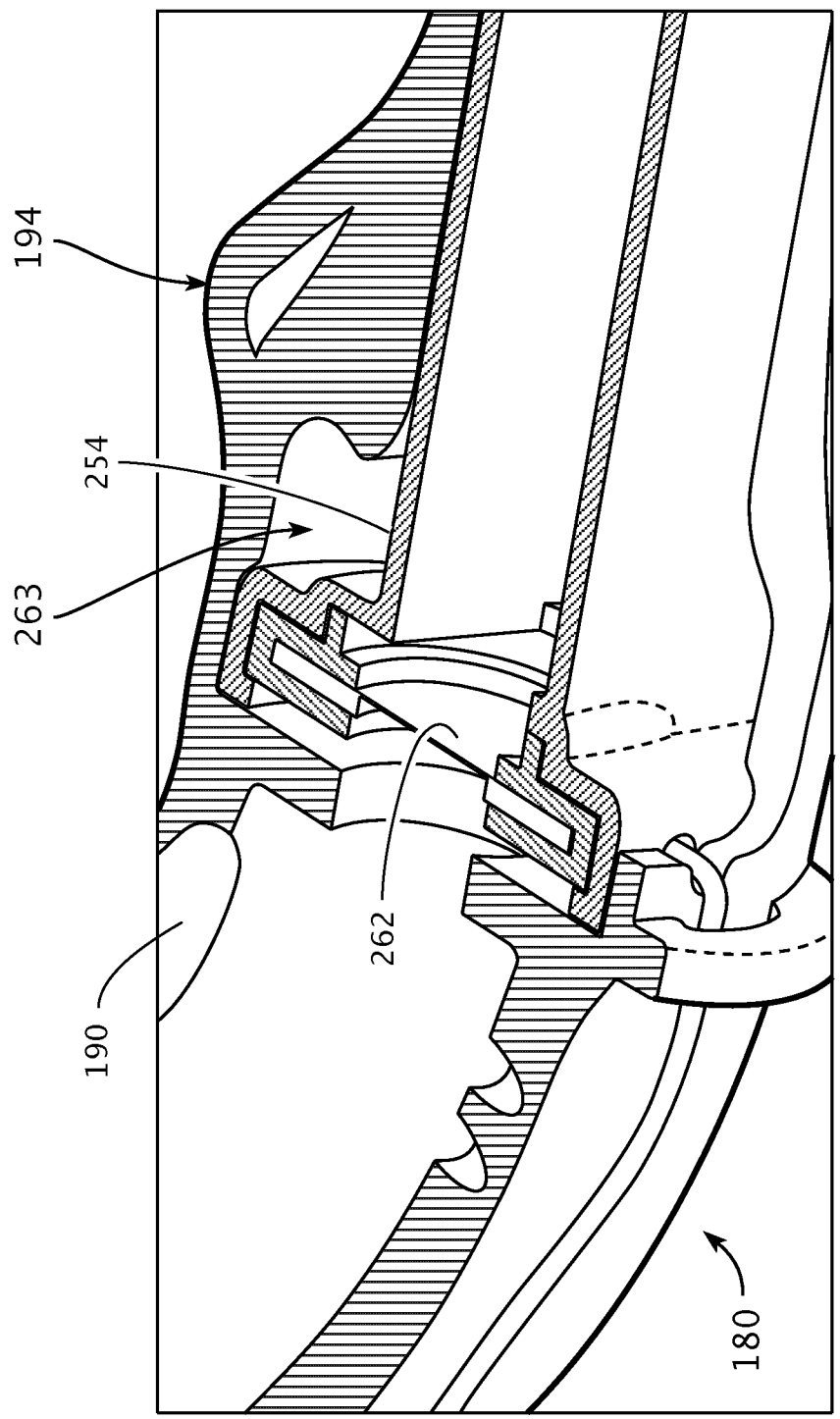
FIG. 5 is a partial cut-away perspective view of a portion of the combination fluid supply and inhalation delivery device.

In an alternative embodiment, as shown in the left-most portion of FIG. 4 and in FIG. 5, the tank/pack 230 includes a ultrasonic piezoelectric transducer/piezoelectric crystal/nebulizer 262 electrically coupled to the battery 228 through electrical wires 229 to vibrate at high frequencies (e.g., 1-3 MHZ) to create a fine cold/cool mist/without heating of liquid in housing/tank/storage 254 involved.

The housing(s)/tank(s)/liquid storage(s) 254 have an elongated rectangular hollow block configuration with a cylindrical disk-shaped head 261 that is received within a cylindrical disk-shaped receiving section 263 of the first leg member 200, which also has an elongated rectangular hollow block configuration, to retain the housing(s)/tank(s) 254 in the first leg member 200.

The removably insertable electronics pack/components 218 in the second leg member 210 includes the circuit board 240, which includes one or more of the air pressure sensor 225, the battery/power source 228, a microprocessor 270 for resistance/temperature calculations, a battery wattage control 275, a Bluetooth microprocessor 290, an amplifier 292 (to increase the battery power to the power needed for the piezoelectric crystal), a Bluetooth module 300, and a USB recharging connector 302 (FIG. 2).

In use, the mask 100 (with device 110 inserted therein) is placed over the lower part of the wearer's face. Inhalation of air through a wearer's nasal passages (or through one's mouth/oral cavity in embodiment of inhalation delivery mechanism 180 with mouthpiece) activates either the vape tank/pack 230, heating oil or solid material therein, thereby creating vapor, releases liquid stored in the tank/pack 230 via a vaporizing nozzle, or activates the ultrasonic piezoelectric transducer 262 to create a fine, cool mist that will enter the wearer's nasal/oral passages.

Vape, delivery, and/or delivery of the fine mist from the housing(s)/tank(s)/liquid storage(s) 254 is designed to have adjustable sensitivity allowing the wearer/wearer to customize the vape/aerosol/mist activation point. The air pressure sensor 225 measures the inhalation pressure and the microprocessor 270 determines if the inhalation pressure meets and/or exceeds a predetermined inhalation pressure/level/vape/aerosol/mist activation point. If the inhalation pressure meets and/or exceeds a predetermined inhalation pressure/level/vape/aerosol/mist activation point, the programmable microprocessor 270 will adjust the amount and/or duration of voltage delivery to vape heating coil 260, electromechanical puncturing device on tank 220, or ultrasonic piezoelectric transducer 262, allowing for precise control of each activation per air intake by wearer. The built-in Bluetooth module 300 coupled with microprocessor 270 allows for functionality control via a mobile app on a mobile computing device (e.g., IPHONE®). This functionality control also allows to control total duration or number of activations per each time the device 110 is used.

In the vape tank/pack 230 example, the microprocessor 270 measures the initial resistance of the vape heating coil 260. Upon heating of the vape heating coil 260, the resistance changes, allowing for a mathematical calculation of the coil temperature within 10 degrees Fahrenheit. Based on measured and programmable information, the battery wattage control module 225 will adjust the wattage delivered by the battery pack 230 to the vape heating coil 260.

In the ultrasonic piezoelectric transducer 262 nebulizer example, the intake of a breath is measured by the air pressure sensor 225, which in turn triggers the ultrasonic nebulizer to atomize the liquid via vibration and without the addition of heat. This produces a fine cold/cool mist that will be inhaled by the wearer.

The mask 100 may include one or more embodiments such as, but not limited to, a vape embodiment including the vape tank and heating coil, nasal pillow (or mouthpiece) inhalation delivery device, air filtration mask, battery and Bluetooth control; a embodiment including canister, mechanical gear and miniature electro motor driven device to temporarily pierce seal on canister, nasal pillow (or mouthpiece) inhalation delivery device, air filtration mask, battery and Bluetooth control; an ultrasonic piezoelectric transducer embodiment including housing/tank 254 with liquid (e.g., water) therein, the ultrasonic piezoelectric transducer, the nasal pillow (or mouthpiece) inhalation delivery device, air filtration mask, battery and Bluetooth control; and an oxygen embodiment including an oxygen (O2) canister, mechanical gear and miniature electro motor driven means to temporarily pierce seal on O2 canister, nasal pillow (or mouthpiece) inhalation delivery device, air filtration mask, battery and Bluetooth control.

In another embodiment, the mask 100 is disposable. In this use, the device 110 would be sold without the Bluetooth connection. All parts would be encased in silicone. The battery 228 would be non-rechargeable. Vape tank, canister, or ultrasonic piezoelectric transducer canister would be one-time use, non-replaceable, and non-refillable.

In a further "full suite" embodiment, the device 110 would be either a vape, an aerosol, or an ultrasonic piezoelectric transducer version and include a rechargeable battery, and have replaceable or refillable tanks/housing(s). In this embodiment, there would be full Bluetooth connection via a mobile device app on one's mobile device.

In further embodiments/implementations, the one or more components described and/or shown herein are held in position on the wearer's face by a means other than a mask.

In one or more further embodiments/implementations, additional applications for the device 110 are, but not limited to: to act as a wearable humidifier by supplying fine purified water mist; to dispense to the wearer any number of vitamin(s), essential oil(s), and other non-prescription medicinal liquids (added for example to the purified water), and/or to allow prescription medications that are currently administered in hand held nebulizers, such as asthma medication, to be administered to the wearer "on demand" and hands free.

Figure 7:
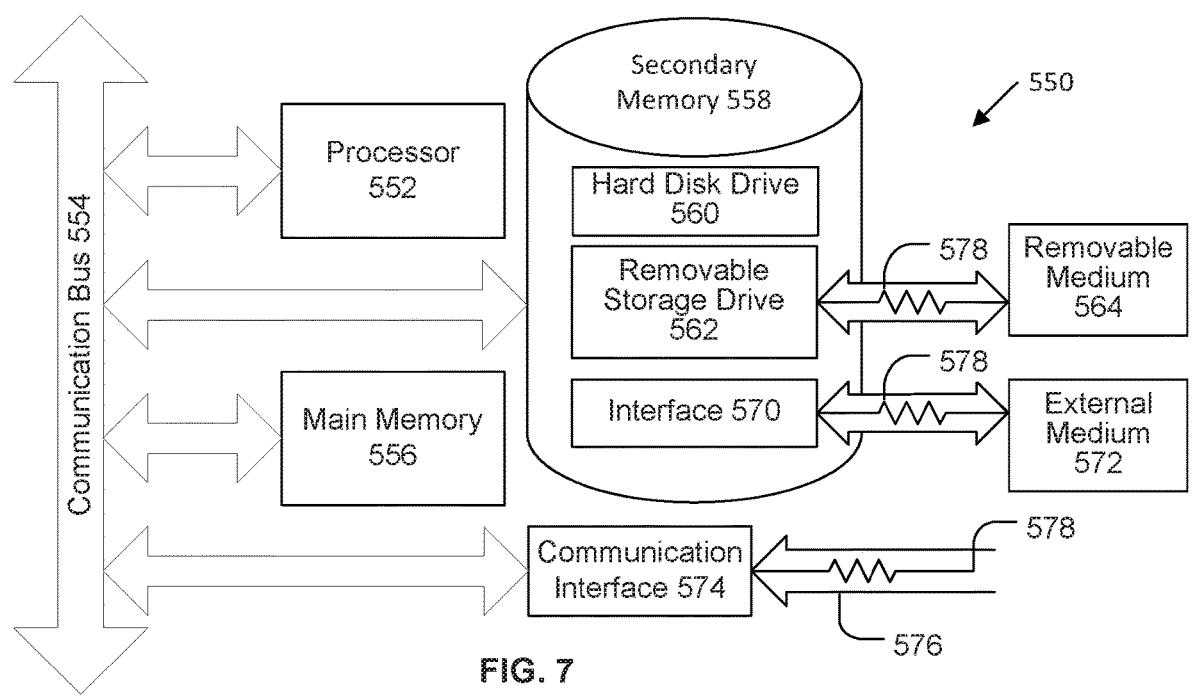
FIG. 7 is a block diagram illustrating an example computer system that may be used in connection with various embodiments described herein.

FIG. 7 is a block diagram illustrating an example computer system 550 that may be used in connection with various embodiments described herein. For example, the computer system 550 may be used in conjunction with control and/or operation of the device 110 and/or mobile device app for control and/or operation of the device 110. However, other computer systems and/or architectures may be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link (e.g., Bluetooth® wireless data communication link), radio frequency (RF) link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

While various embodiments of the present invention have been described above, it should be understood that they have been presented by way of example only, and not of limitation. Likewise, the various diagrams may depict an example architectural or other configuration for the disclosure, which is done to aid in understanding the features and functionality that can be included in the disclosure. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

The invention claimed is:

1. A wearable inhalation delivery device, comprising:
a wearable member that is securable to a wearer's head;
an inhalation delivery device carried by the wearable member and configured to deliver a fluid to the wearer's air passages upon inhalation,
wherein the inhalation delivery device includes opposite laterally extending leg members comprising a first leg member having a supply, the first leg member includes a side with a flexible opening that the supply is removably insertable within.

2. The wearable inhalation delivery device of claim 1, wherein the first leg member has a cylindrical disk-shaped receiving section and the supply includes a cylindrical disk-shaped head that is received within the cylindrical disk-shaped receiving section of the first leg member to retain the supply in the first leg member.

3. A wearable inhalation delivery device, comprising:
a wearable member that is securable to a wearer's head;
an inhalation delivery device carried by the wearable member and configured to deliver a fluid to the wearer's air passages upon inhalation,
wherein the inhalation delivery device includes opposite laterally extending leg members comprising a first leg member having a supply and a second leg member having an electronics pack.

4. The wearable inhalation delivery device of claim 3, wherein the second leg member includes an open end that the electronics pack is removably insertable within.

5. The wearable inhalation delivery device of claim 4, wherein the inhalation delivery device includes an air pressure sensor, a power source, and a microprocessor configured to deliver to the wearer's air passages upon detection of inhalation by the air pressure sensor.

6. The wearable inhalation delivery device of claim 5, wherein the inhalation delivery device includes a vape tank with a vape heating coil, the microprocessor configured to determine coil temperature based in part on measured resistance of the vape heating coil and control the power source to adjust supply of power to the heating coil to control an amount of vape delivered.

7. The wearable inhalation delivery device of claim 5, wherein the inhalation delivery device includes a tank and a vaporizing nozzle, and the microprocessor is configured to control the vaporizing nozzle to control an amount of fluid released from the tank.

8. The wearable inhalation delivery device of claim 5, wherein the inhalation delivery device includes an oxygen tank and a mechanism to release oxygen from the oxygen tank, and the microprocessor is configured to control the mechanism to control an amount of oxygen released from the oxygen tank.

9. The wearable inhalation delivery device of claim 5, wherein the inhalation delivery device includes a fluid tank and an ultrasonic piezoelectric transducer, and the microprocessor is configured to control the ultrasonic piezoelectric transducer to control an amount of fine mist released from the fluid tank.

10. The wearable inhalation delivery device of claim 5, wherein the air pressure sensor is configured to measure inhalation pressure and if the microprocessor determines if the inhalation pressure has at least met a minimum predetermined inhalation pressure to deliver fluid.

11. The wearable inhalation delivery device of claim 5, wherein the inhalation delivery device includes electronics and a module coupled with the microprocessor to allow functionality control of the inhalation delivery device via a mobile app on a mobile computing device.

12. A wearable inhalation delivery device, comprising:
a wearable member that is securable to a wearer's head;
an inhalation delivery device carried by the wearable member and configured to deliver a fluid to the wearer's air passages upon inhalation,
wherein the inhalation delivery device is configured to span the wearer's face and includes an electronics pack, an air pressure sensor, a power source, and a microprocessor, the inhalation delivery device configured to deliver the fluid to the wearer's air passages upon detection of inhalation by the air pressure sensor, and the air pressure sensor is configured to measure inhalation pressure and if the microprocessor determines the inhalation pressure has at least met a minimum predetermined inhalation pressure to deliver fluid.

13. The wearable inhalation delivery device of claim 12, wherein the inhalation delivery device includes a vape tank with a vape heating coil, the microprocessor configured to determine coil temperature based in part on measured resistance of the vape heating coil and control the power source to adjust supply of power to the heating coil to control an amount of vape delivered.

14. The wearable inhalation delivery device of claim 12, wherein the inhalation delivery device includes a tank and a vaporizing nozzle, and the microprocessor is configured to control the vaporizing nozzle to control an amount of fluid released from the tank.

15. The wearable inhalation delivery device of claim 12, wherein the inhalation delivery device includes an oxygen tank and a mechanism to release oxygen from the oxygen tank, and the microprocessor is configured to control the mechanism to control an amount of oxygen released from the oxygen tank.

16. The wearable inhalation delivery device of claim 12, wherein the inhalation delivery device includes a fluid tank and an ultrasonic piezoelectric transducer, and the microprocessor is configured to control the ultrasonic piezoelectric transducer to control an amount of fine mist released from the fluid tank.

17. The wearable inhalation delivery device of claim 12, wherein the inhalation delivery device includes electronics and a module coupled with the microprocessor to allow functionality control of the inhalation delivery device via a mobile app on a mobile computing device.

18. A wearable inhalation delivery device, comprising:
a wearable member that is securable to a wearer's head;
an inhalation delivery device carried by the wearable member and configured to deliver a fluid to the wearer's air passages upon inhalation,
wherein the inhalation delivery device includes an electronics pack, an air pressure sensor, a power source, a microprocessor, the inhalation delivery device configured to deliver the fluid to the wearer's air passages upon detection of inhalation by the air pressure sensor, and a vape tank with a vape heating coil, the microprocessor configured to determine coil temperature based in part on measured resistance of the vape heating coil and control the power source to adjust supply of power to the heating coil to control an amount of vape delivered.

\* \* \* \* \*